United States Patent [19]

Isaacs

[11] Patent Number: 4,598,057

[45] Date of Patent: Jul. 1, 1986

[54] REGENERATION OF SOLUBLE MOLYBDENUM CATALYSTS FROM SPENT CATALYST STREAMS

[75] Inventor: Bruce H. Isaacs, Newtown Square, Pa.

[73] Assignee: Atlantic Richfield Company, Los Angeles, Calif.

[21] Appl. No.: 665,234

[22] Filed: Oct. 26, 1984

[51] Int. Cl.$^4$ ............... B01J 38/68; C07D 333/02
[52] U.S. Cl. .................... 502/24; 423/53; 502/28; 502/33; 549/529
[58] Field of Search ............ 502/24, 33, 28; 423/53, 423/55; 562/597

[56] References Cited

U.S. PATENT DOCUMENTS

| | | | |
|---|---|---|---|
| 3,351,635 | 11/1967 | Kollar | 502/215 |
| 3,351,635 | 11/1967 | Kollar | 502/215 |
| 3,362,972 | 1/1968 | Kollar | 260/414 |
| 3,434,975 | 3/1969 | Sheng et al. | 502/171 |
| 3,453,218 | 7/1969 | Sheng et al. | 549/529 |
| 3,480,563 | 11/1969 | Bonetti et al. | 252/431 |
| 3,819,663 | 6/1974 | Levine et al. | 549/541 |
| 3,822,321 | 7/1974 | Mavrim | 260/635 H |
| 3,887,361 | 6/1975 | Lempke | 502/33 |
| 4,157,346 | 6/1979 | Lines et al. | 260/348.31 |

FOREIGN PATENT DOCUMENTS

| | | |
|---|---|---|
| 1550166 | 12/1968 | France . |
| 100561 | 3/1979 | Poland . |
| 103742 | 10/1979 | Poland . |
| 1060122 | 2/1967 | United Kingdom . |
| 665234 | 10/1974 | U.S.S.R. . |

OTHER PUBLICATIONS

Journal Less Common Met., vol. 54, pp. 149–152 (1977), "Structure & Catalytic Reactivity of some Bis–Carboxylate of Molybdenum (V) Complexes", by J. Sobczak & J. J. Ziolkowski.

Chemical Abstracts–vol. 73, (1970)–81316q, "Complexing of Molybdenum Lens with Some Dicarboxylic Acids"–by Kuzmina et al.

Primary Examiner—P. E. Konopka
Attorney, Agent, or Firm—Michael S. Jarosz

[57] ABSTRACT

The process of regenerating a stable organic soluble molybdenum-containing catalyst suitable for epoxidation of olefins with a hydroperoxide which comprises thermally precipitating and separating a molybdenum-containing solid obtained from a spent catalyst stream derived from a molybdenum catalyzed epoxidation of an olefin and solubilizing the precipitated solid by contacting with a liquid composition comprising a peroxy compound, a monohydroxy alcohol, optionally a polyhydroxy alcohol, and an organic dicarboxylic acid present in an amount of at least about 0.2 parts, by weight, of molybdenum contained in said solid.

14 Claims, No Drawings

REGENERATION OF SOLUBLE MOLYBDENUM CATALYSTS FROM SPENT CATALYST STREAMS

BACKGROUND OF THE INVENTION

The production of oxirane compounds, such as propylene oxide and its higher homologs, is described in Kollar U.S. Pat. No. 3,351,635. In accordance with the Kollar process, the oxirane compound may be prepared by epoxidation of an olefinically unsaturated compound (for example, propylene) by use of organic hydroperoxide and a suitable metal catalyst, such as a molybdenum compound. Kollar teaches that activity of the metal catalyst disclosed therein for expoxidation of primary olefins is high and can lead to high selectivity of propylene to propylene oxide. These selectivities are obtained at high conversions of hydroperoxide (50% or higher) which conversion levels are important for commercial utilization of this technology. In accordance with the Kollar process, the epoxidation reaction proceeds under pressure in a liquid state, and accordingly, a liquid solution of the metal catalyst is desired.

In the preparation of metal compounds, for example, molybdenum salts, for the aforementioned purposes, various techniques have been used, many of which have been found to be extremely difficult to carry out efficiently on a commerical scale, and hence expensive, particularly for preparing hydrocarbon soluble compositions containing a high molybdenum content. Kollar U.S. Pat. No. 3,362,972 is concerned with preparation of molybdenum salts of carboxylic acids wherein molybdenum trioxide is reacted with oxalic acid in the presence of hexanoic acid. Sheng et al. U.S. Pat. No. 3,434,975 reports the preparation of molybdenum containing catalysts by reaction of molybdenum metal with peroxy compounds in the presence of a saturated alcohol. Sheng et al. U.S. Pat. No. 3,453,218 discloses the preparation of molybdenum containing epoxidation catalysts by reaction of molybdenum metal with a combination of tertiary butyl hydrogen peroxide and formic acid at low temperature. Ziolkowski et al. Polish Pat. No. 100,561 discloses the preparation of molybdenum-containing catalysts by treating $Mo(OH)_5$ with certain aliphatic or dicarboxylic acids and with an alpha-hydroxy acid or with certain diols or beta-diketones in an organic solvent. Ziolkowlski et al. Polish Pat. No. 103,742 is concerned with preparation of complexes of molybdenum from $Mo(O)(OH)_3$ and oxalic acid, lactic acid and ethylene glycol deposited on certain carriers. Sobczak et al., *Journal Less-Common Met.*, Vol. 54, pp. 149–52 (1977) describe the reaction of molybdenum complexes with dicarboxylic acids, such as oxalic acid. Finally, Kuzimina et al., *Izv. Trimiryazev. Sel'skokhoz Akad.* (2), 224–8 (1970) describe complex forming reactions of molybdenyl ions with certain organic dicarboxylic acids, including oxalic acid.

However, each of these prior art processes are deficient by requiring expensive starting materials or forming carboxylates or complex molybdenum compositions which contain relatively low metal content and/or in requiring a number of steps in order to produce the desired high molybdenum-containing soluble catalyst composition.

Another molybdenum epoxidation catalyst is described by Bonetti et al in U.S. Pat. No. 3,480,563. Bonetti teaches that molybdenum trioxide may be reacted with a primary saturated acyclic alcohol having 4 to 22 carbon atoms or with a mono- or polyalkylene glycol monoalkyl ether. The reaction involves heating the molybdenum trioxide in the alcohol or ether to produce an organic soluble molybdenum catalyst.

Maurin et al in U.S. Pat. No. 3,822,321 describe oxidizing olefins with a hydroperoxide using a molybdenum catalyst prepared by reacting a molybdenum compound such as molybdic acid or a molybdic salt with a polyalcohol.

A molybdenum catalyzed epoxidation of olefins is described by Lines et al in U.S. Pat. No. 4,157,346. The catalyst is prepared by reacting an oxygen containing molybdenum compound with an amine (or an amine N-oxide) and alkylene glycol.

British Pat. No. 1,060,122 is concerned with an epoxidation reaction employing catalytic quantities of a molybdenum catalyst which is in the form of an inorganic molybdenum compound.

French Pat. No. 1,550,166 discloses that molybdic acid esters, and especially the glycol esters of molybdic acid, provide certain advantages over previously known catalysts to effect epoxidation employing organic hydroperoxides for reaction with olefinic compounds.

In U.S. Pat. No. 3,887,361 Lemke discloses that spent catalyst solutions obtained from the process of epoxidation of olefins with hydroperoxides in the presence of molybdenum may be treated to precipitate and separate dissolved molybdenum. The Lemke process involves mixing spent catalyst solution with 5 to 50 parts by weight of tertiary-butyl alcohol and heating the mixture to between 100° C. and 300° C. in a closed vessel or under reflux, thereby resulting in precipitation of molybdenum as a finely divided solid. The solid is disclosed to be suitable for recycle into further epoxidation reactions, as such, or optionally, after dissolution in an organic acid or an acid obtained in the "Oxo process" for production of oxygenated organic derivatives. The Lemke solids typically contain about 30 to about 40 percent by weight of molybdenum.

Accordingly, it is an object of the present invention to provide a simple, inexpensive method for the regeneration of molybdenum compositions from spent molybdenum-containing solid catalysts which compositions are characterized by a high metal content and are suitable for re-use in the epoxidation of olefins with organic hydroperoxides to produce the corresponding oxirane compounds.

A further object of the present invention is to provide a process for the preparation and/or reuse of molybdenum-containing epoxidation catalysts from spent molybdenum catalyst compositions which process is characterized by reduced hydroperoxide consumption and molybdenum losses and improved catalyst preparation productivity.

SUMMARY OF THE INVENTION

It has been discovered that spent solid molybdenum catalysts can be effectively regenerated in a stable, soluble form and reused in the epoxidation of olefins. In accordance with the present invention, the method of regenerating soluble molybdenum catalyst for epoxidation of olefins with a hydroperoxide comprises thermally precipitating and separating a molybdenum-containing solid from a spent catalyst solution obtained from the molybdenum catalyzed epoxidation of an olefin and solubilizing the precipitated solid by contacting with a peroxy compound, such as an organic hydroperoxide, organic peracid, or hydrogen peroxide, or admixtures thereof, and a certain organic dicarboxylic acid in the presence of a monohydroxy alcohol and optionally, in the presence of an additional secondary solvent, such as a polyhydroxy alcohol. This discovery is deemed surprising since it is known in the art, for example from British Patent No. 1,060,122 and from Levine et al U.S. Pat. No. 3,819,663, that it is desirable to exclude acids from such epoxidation systems since acid impurities, such as carboxylic acids, destablize molybdenum-containing catalyst solutions or interefere with the epoxidation reaction in which the molybdenum-containing catalyst composition is employed. This improved result is achieved without being accompanied by deleterious corrosion, normally accompanied by the presence of acidic components in chemical process applications. In addition, it has also been found that the high molybdenum containing catalyst composition solutions of the invention, provide higher yields in epoxidation of olefins with organic hydroperoxides to the desired alkylene oxide compounds, under the same process conditions, than catalyst compositions prepared in the absence of organic dicarboxylic acid; this discovery is further surprising, since it is known that the presence of acids decreases the yield to desired alkylene oxide product.

The molybdenum-containing catalyst compositions of the invention may be employed in the aforestated epoxidation reaction as fresh stable catalyst solutions, or admixed with the evaporation residue obtained from the previous epoxidation of an olefinic compound with an organic hydroperoxide in the presence of a molybdenum epoxidation catalyst, to a wiped film evaporation at elevated temperatures in accordance with the method described and claimed in the above-identified Levine et al U.S. Pat. No. 3,819,663, the disclosure of which is hereby incorporated by reference.

As used in the present specification and the annexed claims, the term "stable catalyst solution" is intended to mean a molybdenum-containing solution which will not precipitate an appreciable amount, less than about 1% of the molybdenum contained in the solution, of molybdenum, upon heating to a temperature of about 85° C. over a period of at least about four hours.

The present discovery makes it possible to continuously regenerate, recycle and reuse molybdenum catalyst in a continuous process for molybdenum catalyzed epoxidation of olefins with a hydroperoxide by thermally precipitating and separating a molybdenum-containing solid from a spent catalyst solution obtained from a molybdenum catalyzed olefin epoxidation and solubilizing the precipitated solid in a liquid composition comprising an admixture of peroxy compound, monohydroxy alcohol, optionally, a polyhydroxy alcohol, and a certain organic dicarboxylic acid by contacting the solid with such composition to produce an active catalyst solution, and adding a catalytic amount of the active solution to a hydroperoxide epoxidation of an olefin.

As used in the present specification and the annexed claims, the term "spent catalyst solution" is intended to mean that fraction of the epoxidation reaction product effluent remaining after removal, by a series of fractionation steps, in conventional manner, of unreacted olefin (for example, propylene), alkylene oxide (for example, propylene oxide), and a major portion of the alcohol corresponding to the hyderperoxide (for example, tertiary butyl hydroperoxide) used in the epoxidation reaction which reaction may be according to the procedure of Kollar U.S. Pat. No. 3,351,635, the disclosure of which is hereby incorporated by reference. Spent catalyst solution, which may contain molybdenum at levels of up to about 5 percent by weight, contains some alcohol, acids and other low molecular weight oxygenated compounds; said spent catalyst solution is generally not subjected to any chemical treatment before being subjected to the process of the present invention. It is contemplated that spent catalyst solution, as used herein, includes both the distillation bottoms treated in British Patent Specification No. 1,317,480 and the residue obtained from the wiped film evaporation process according to Levine U.S. Pat. No. 3,819,663, the disclosures of which are also hereby incorporated by reference.

Solid precipitates of molybdenum-containing compounds are obtained from spent catalyst solutions by a variety of methods. The present invention relates to a process for dissolving those solids to produce an active, stable, soluble epoxidation catalyst for use in processes such as those taught by Kollar. Accordingly, the present invention permits substantially complete recycle of catalyst values to the epoxidation zone and avoids the necessity of disposal of spent molybdenum catalyst solutions which is detrimental from both economic and ecological view points. These and other objects of the invention will become apparent from the following description and examples.

DETAILED DESCRIPTION OF THE INVENTION

In general, the molybdenum catalyzed hydroperoxide epoxidation crude reaction product evolving from processes such as described in the aforementioned Kollar patent, is subjected to a series of fractionation steps whereby there are consecutively separated, as distillate, unreacted olefin, alkylene oxide and the alcohol corresponding to the hydroperoxide. The remaining residue, a heavy organic liquid bottoms stream, contains high boiling by-products and dissolved molybdenum catalyst.

This heavy liquid bottom stream from the last of the above-named distillations comprises the spent catalyst solution which serves as a starting material in the process of the present invention. Normally, this stream contains up to about 10 percent by weight of the alcohol corresponding to the hydroperoxide; for purposes of this invention, this alcohol content is not critical and can vary widely. Also contained in said heavy fraction are formic acid, acetic acid, propylene glycol, dipropylene glycol, glycol ethers and water which are impurities formed in small but still significant quantities, usually during the epoxidation. The heavy fraction also contains a molybdenum epoxidation catalyst in the form of an organic complex mixture which is soluble in the said liquid fraction.

As indicated above, this heavy fraction cannot be recycled directly to the epoxidation zone in view of the fact that the impurities contained therein, and most notably the acid impurities, interfere with the epoxidation reaction. The deleterious effect of these acids is particularly pronounced in a continuous system due to a build-up of the concentration of these materials when a direct recycle is employed. Furthermore, partial recycle of the stream to the epoxidation reaction, over a period of time, results in accumulation of residual materials associated with the catalyst which likewise is deleterious to the overall epoxidation reaction. Nor can the heavy stream be directly burned in order to utilize the heat content thereof, since in such an operation the molybdenum is converted to molybdenum trioxide which settles out on surfaces in the furnace interfering with and ultimately interrupting the furnace operation. Environmental disadvantages are also clearly apparent in any such burning operation.

In accordance with the present invention, the spent catalyst solution, i.e., heavy fraction as described above, is subjected to a thermal treatment thereby precipitating a molybdenum-containing solid from said spent catalyst stream and separating the undesired acidic compounds which are deleterious in the epoxidation reaction from the molybdenum-containing precipitated solid. Customary and regular procedures cannot be employed in accomplishing a resolution of this heavy fraction in view of the tendency of the molybdenum-containing residue to cake, coat and plug conventional apparatus. Thereafter, the precipitated solid molybdenum-containing composition is solubilized by direct reaction with a peroxy compound and a certain organic dicarboxylic acid in the presence of a monohydroxy alcohol; or optionally an admixture of a monohydroxy alcohol with a polyhydroxy alcohol, present as a diluent in the formulation of the desired molybdenum-containing catalyst composition.

As part of the invention, one of several procedures for effecting thermal precipitation of the molybdenum containing solid from spent catalyst solution may be carried out. In the first of these procedures, the process described in Lemke U.S. Pat. No. 3,887,361, referred to above, may be employed; this process comprises heating the spent catalyst solution with from about 5 to 50 percent by weight of tertiary butyl alcohol to a temperature between about 100° C. to 300° C. in a closed vessel or under reflux and thereafter separating the resulting precipitate containing substantially all the molybdenum originally present in the distillation residue. A second procedure for effecting such thermal treatment involves admixing the spent organic catalyst solution with water in an amount between about 0.5 and 10 percent based on the weight of the organic solution and heating the resultant admixture to a temperature in the range of between about 150° C. and 250° C. under pressure sufficient to maintain the admixture in liquid phase and for a time sufficient to precipitate at least a portion of the molybdenum contained in the organic solution as a solid, and thereafter separating the precipitated molybdenum-containing solid from the organic solution, as described and claimed in copending application Ser. No. 227,115 of R. B. Poenisch, entitled "Process for the Recovery of Molybdenum from Organic Solutions", filed Jan. 21, 1981, and in Dugua U.S. Pat. No. 4,317,802, issued Mar. 2, 1982. The disclosures of the Lemke et al and Dugua patents, and of the Poenisch application are hereby incorporated herein by reference.

Another method for separation of molybdenum-containing solid from the spent catalyst solution involves thermal precipitation procedure disclosed and claimed in copending application Ser. No. 227,114, of M. T. Mocella entitled "Production of a Solid Molybdenum Precipitate from a Spent Molybdenum Epoxidation Catalyst Solution", filed Jan. 21, 1981. This method comprises removing and recovering dissolved molybdenum as a molybdenum-containing solid by admixing the spent catalyst solution with water in an amount sufficient to produce a two-phase system comprising an organic phase and an aqueous phase, heating the resultant aqueous phase which is rich in molybdenum values to precipitate the molybdenum-containing solid and separating the solid; the disclosure of this application Ser. No. 227,114 is also hereby incorporated herein by reference.

The solid molybdenum-containing precipitate resulting from any of the aforementioned thermal precipitation procedures may contain up to about 50, and generally, up to about 40 weight percent molybdenum, by weight. Reuse of the molybdenum contained in the solid precipitate resulting from said thermal treatment requires an efficient method to solubilize the molybdenum so that a high quality epoxidation may be achieved.

The organic hydroperoxides which are employable in the present invention are characterized by being liquid at the reaction conditions employed and by having the structure ROOH, wherein R may be alkyl, alkenyl, aryl, alkaryl, aralkyl, cycloalkyl, cycloalkenyl and similar radicals which also contain functional groups. Examples of such hydroperoxide employable in the preparation of the molybdenum-containing catalyst of the invention include tertiary butyl hydroperoxide, tertiary amyl hydroperoxide, cumene hydroperoxide, tetralin hydroperoxide, alphahydroperoxy diisopropylketone, the hydroperoxide of 2-methylbutene-2, the hydroperoxide of octene-1, the hydroperoxide of 2,6-di-tertiary butyl paracresol, and the like. Tertiary butyl hydroperoxide is preferred since, upon reduction, it is converted into the corresponding alcohol which is a convenient solvent for the epoxidation reaction, when propylene, for example, is employed as the starting olefin. When the peroxy compound is employed as an organic hydroperoxide, such hydroperoxide is preferably present in the form of a 30 to 40 percent, by weight, solution thereof. Included among the various peracids which may be utilized are performic acid, peracetic acid, trifluoroperacetic acid, perbenzoic acid and the like; of these, peracetic acid is particularly preferred.

The organic dicarboxylic acids employable in regeneration of the molybdenum-containing catalyst compositions of the invention include aliphatic, cycloaliphatic and aromatic dicarboxylic acids of from 2 to 18 carbon atoms, preferably, 2 to 8 carbon atoms in the case of aliphatic and cycloaliphatic dicarboxylic acids, and 8 to 12 carbon atoms in the case of aromatic dicarboxylic acids. Organic dicarboxylic acids of such character which contain the carboxylic acid groups on adjacent carbon atoms are particularly preferred. Illustrative examples of suitable organic dicarboxylic acids employable herein include oxalic acid, malonic acid, succinic acid, glutaric acid, adipic acid, maleic acid, fumaric acid, phthalic acid, isophthalic acid, terephthalic acid, and 1,2-naphthalene dicarboxylic acid. Oxalic and phthalic acid constitute particularly preferred species of employable organic dicarboxylic acids in preparation of the catalyst compositions of the present invention.

Suitable monohydroxy alcohols employable in formulation of the liquid catalyst composition of the invention include aliphatic alcohols of 1 to 12 carbon atoms, preferably 4 to 10 carbon atoms. Although the monohydroxy compound employable herein may be substituted with functional groups which are inert to the reactants present, for example, halo-, such as chloro or fluoro; nitro; cyano; carbonyl; and carboxyl, the readily available aliphatic monohydroxy-containing organic compounds containing only carbon, hydrogen and oxygen are particularly satisfactory for use in the present invention. Illustrative suitable monohydroxy compounds include methanol, ethanol, propanol, n-hexanol, 2-ethylhexanol and particularly preferred is tertiary butyl alcohol. The monohydroxy alcohol portion of the admixture is generally adjusted so that sufficient monohydroxy alcohol is introduced to provide the maximum concentration of molybdenum in the form of a stable solution in accordance with the invention. In general, the monohydroxy alcohol is employed in amount of at least about 25 and, preferably between about 50 and 200, parts per part of molybdenum, to be solubilized.

The polyhydroxy compound suitable for use in formulation of the aforementioned molybdenum-catalyst compositions, if employed, also generally contain up to about 12 carbon atoms. Such polyhydroxy compounds normally contain 2 to 4 hydroxyl groups, but preferably contain 2 hydroxyl groups, i.e., monoalkylene glycols or derivatives thereof, such as glycol ethers, provided these compounds contain at least one hydroxyl group. As is the case in connection with the monohydroxy alcohol referred to above, the polyhydroxy compounds may be substituted with functional groups which are inert to the reactants present. Polyhydroxy compounds containing solely carbon, hydrogen and oxygen are particularly preferred. Typical illustrative polyhydroxy compounds employable in preparation of the catalyst compositions of the invention include ethylene glycol, propylene glycol, butylene glycols such as 1,4-butanediol, catechol and alkylene ethers of such glycols, including the methyl and ethyl ethers thereof. In general, when the diluent comprises an admixture of monohydroxy and polyhydroxy alcohols, the polyhydroxy alcohol is employed in an amount of up to about 25 percent, preferably up to about 10%, by volume, of the monohydroxy alcohol employed. However, large excesses of polyhydroxy alcohol should be avoided since such compounds have a deleterious effect on subsequent epoxidation reactions, and hence, large excesses are not favored for molybdenum solubilization.

The quantities of reactants employed in formulation of the molybdenum-containing compositions of the invention may be varied over wide ranges. In general, the weight ratio of thermally precipitated molybdenum solid to peroxy compound, illustratively, an organic hydroperoxide, such as tertiary butyl hydroperoxide, may range from about 1:2 to 1:20, with ranges of 1:10 to 1:15 being preferred. The weight ratio of thermally precipitated molybdenum-containing solid to monohydroxy alcohol also may vary over wide limits, the preferred range being, however, from about 1:50 to 1:200. When an admixture of monohydroxy and polyhydroxy alcohols is employed, the ratio of molybdenum-containig solid to monohydroxy alcohol may be as low as 1:4 to 1:100, with from about 75 to 99 weight percent of the total alcohol present being a monohydroxy alcohol. In general, the organic dicarboxylic acid is employed in amount ranging from about 0.2 to 4 moles, preferably 0.5 to 2.0 moles per mole of molybdenum to be solubilized. The final molybdenum-containing catalyst composition of the invention is characterized by containing of from about 0.1 to about 3 percent of molybdenum by weight, preferably from about 0.5 to about 2 percent, molybdenum, by weight.

The temperature employed to solubilize the thermally precipitated molybdenum solid in formulation of the catalyst of the molybdenum-catalyst compositions in the invention may range between about 20° C. and about 130° C., and preferably between about 50° C. and about 100° C. Temperatures lower than about 20° C. necessitate unduly long reaction times and are not favored. A particularly convenient temperature is the reflux temperature of the liquid admixture into which the molybdenum solid is being solubilized. In general, atomspheric pressure for the solubilization reaction is suitable, although the reaction may be carried out at superatomspheric pressures when necessary to maintain the reaction mixture in the liquid phase. When the reaction is carried out at higher temperatures which would cause vaporization of the alcohol, sufficient pressure is used to maintain the liquid phase: for example, in the event methanol is employed as the monohydroxy alcohol component, use of temperatures higher than about 60° C. require that super atmospheric pressure be used to maintain the liquid state.

The time required to solubilize the thermally precipitated molybdenum solid to a stable active solution is a function of both temperature, and nature and proportions of components of the mixture. Generally, solubilization requires a reaction time ranging from a few minutes, for example, 15 minutes at the higher temperatures, to several hours at the lower temperatures, with reaction times in the range of from about 30 minutes to 2 hours being preferred when the preferred temperature range is employed.

The molybdenum-containing catalyst composition is prepared in accordance with the process of the present invention have been found to be suitable for epoxidation of olefins, illustratively propylene, to produce the corresponding oxirane compound, propylene oxide, for example, at high yields and conversions, without production of undesirable high quantities of undesirable by-products. In general, the catalyst composition of present invention is suitable for the epoxidation of compounds having the general formula:

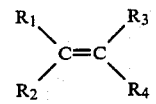

where $R_1$, $R_2$, $R_3$ and $R_4$ may be hydrogen, alkyl, aryl arylalkyl, alkaryl, alkenyl, alkadienyl or similar radicals having functional groups, in accordance with the process described and claimed in Kollar U.S. Pat. No. 3,351,635. Illustrative acyclic olefinic hydrocarbons which may be epoxidized are the aliphatic normally gaseous olefins such as propylene, the butylenes and the higher olefins, including the liquid and high molecular weight solid olefins. Mono-olefinic hydrocarbons, di-olefinic hydrocarbon and polyolefinic hydrocarbons may also be epoxidized by the catalyst of the present invention.

In addition to being employed as fresh catalyst solution in the above-described epoxidation reaction, the molybdenum-containing catalyst composition of the present invention finds particular use when employed together with molybdenum-containing catalyst concentrates or residues obtained from previous epoxidation processes employing a molybdenum epoxidation catalyst; in such operations, the epoxidation reaction mixture is resolved into product fractions, including a heavy liquid fraction containing the catalyst, subjecting such heavy liquid fraction to evaporation, such as a wiped film evaporation, at elevated temperatures until at least about 60% by weight of said fraction is evaporated overhead, and recycling the evaporation residue to the epoxidation reactions, as described and claimed in Levine et al U.S. Pat. No. 3,819,663, the disclosure of which is hereby incorporated by reference. When employed in such manner, the catalyst composition of the present invention is employed in quantities up to about 90 percent and preferably up to about 50 percent, by weight, of the total molybdenum containing composition required in the epoxidation reaction.

It is desirable to avoid adding excess hydroxyl containing compounds to the epoxidation reaction when solubilized regenerated molybdenum catalyst of the present invention is employed. Accordingly, after the solubilization of thermally precipitated solids, it may be desirable to concentrate the molybdenum in solution, particularly if substantial quantities of primary alcohol are employed in the dissolution reaction. This is conveniently achieved by distilling the solution to remove excess monohydroxy alcohol. While additional solubilizing agents other than those specifically mentioned hereinabove in connection with the liquid composition admixture are not required, optionally, other solubilizing compounds known to those skilled in the art may be employed. In addition, conventional, physical purification procedures may be adopted as an extension of the process of the invention for purposes of effecting purification of the catalyst composition produced in accordance with this process; for example, prior to recycle of the active molybdenum soluble catalyst solution, this liquid may be subjected to filtration to remove any included undesired solid materials.

In order to illustrate practice of the invention, the following examples are provided. However, it is to be understood that the examples are merely illustrative and are not intended as being restricted of the invention herein disclosed and as defined by the next claims. Parts and percentages are by weight, and temperatures are in degrees Centigrade, unless otherwise specified.

EXAMPLE I

A spent catalyst stream from a commercial molybdenum catalyzed epoxidation of propylene, as described in Kollar, U.S. Pat. No. 3,351,635, is thermally treated according to the method set forth in Lemke U.S. Pat. No. 3,887,361 to precipitate dissolved molybdenum as a dark, blue solid. In accordance with this method, the residual organic effluent derived from the process of epoxidation of propylene is heated with about 7% by weight of tertiary butyl alcohol at a temperature ranging from 170° to 215° over a 3 hour period at a pressure building up to about 500 psig.

A mixture of 1.4 parts of thermally precipitated molybdenum-containing solid (equivalent to 11,000 ppm molybdenum), 40 parts of tertiary butyl alchol, 9 parts of a solution comprised of about 40% by weight of tertiary butyl hydroperoxide in tertiary butyl alcohol and 0.72 parts of oxalic acid dihydrate is refluxed over a period of four hours (about 85° C.). Analysis of the resultant solution reveals that no precipitated solids are formed and that the entire charge of 11,000 ppm molybdenum is solubilized in the reaction mixture.

EXAMPLE II

A thermally precipitated molybdenum-containing solid is obtained from a spent catalyst solution from a commercial propylene epoxidation as in Example I. To regenerate that molybdenum-containing solid as a reusable soluble molybdenum catalyst, 0.93 parts of the solid is reacted with 0.49 parts of oxalic acid dihydrate, 27 parts of tertiary butyl alcohol (TBA), 5.0 parts of a solution oxidate comprised of about 40% by weight tertiary butyl hydroperoxide in tertiary butyl alcohol and 1.03 parts of reagent grade propylene glycol (MPG) by heating the reactants together at 90° for 2 hours. The solution obtained after reaction contains 11,000 ppm of dissolved molybdenum which represents 100% of the molybdenum charged.

EXAMPLE III

A mixture of 1.4 parts of thermally precipitated molybdenum solid as obtained in Example I, above, (equivalent to 11,000 ppm molybdenum), 4.4 parts of propylene glycol, 12 parts of a solution comprised of about 40% by weight of tertiary butyl hydroperoxide in tertiary butyl alcohol, 1.4 parts of oxalic acid dihydrate and 31.6 parts of tertiary butyl alcohol is refluxed for four hours at atmospheric pressure (about 85°). Analysis of the resultant solution indicates that no precipitated solids were formed and that the entire charge of 11,000 ppm molybdenum is solubilized in the reaction mixture.

In contrast, replacement of the oxalic acid dihydrate charged with tertiary butyl alcohol results in solubilizing only 6,500 ppm of molybdenum, of the 11,000 ppm charged, after refluxing for four hours at atmospheric pressure.

EXAMPLE IV

A mixture of 1.4 parts of thermally precipitated molybdenum solid as obtained in Example I, above, (equivalent to 11,000 ppm molybdenum) 0.72 parts of oxalic acid dihydrate, 36.7 parts of tertiary butyl alcohol and 12 parts of a solution comprised of about 40% by weight of tertiary butyl hydroperoxide in tertiary butyl alcohol is refluxed for four hours and heated overnight at 50°. Analysis of the resultant product indicated that 11,000 ppm of charged molybdenum was solubilized in the reaction mixture.

In contrast, replacement of the oxalic acid dihydrate with tertiary butyl alcohol results in solubilizing only 1,000 ppm of molybdenum, of the 11,000 ppm charged, after four hours of reflux and heating overnight (16 hours) at 50°.

EXAMPLE V

A catalyst solution is prepared by blending 8.25 parts of thermally precipitated molybdenum solid as obtained in Example I, above, 144 parts of a solution comprised of about 40% by weight tertiary butyl hydroperoxide in tertiary butyl alcohol, 2.7 parts of propylene glycol and 426 parts of tertiary butyl alcohol and heating the blended mixture at reflux temperature for 2 hours. Thereafter the resultant solution is filtered to remove any undissolved solids.

A stainless steel autoclave equipped with a stirrer is charged with 60 parts of propylene, 87 parts of a solution comprised of about 40% by weight tertiary butyl hydroperoxide in tertiary butyl alcohol and 3 parts of a catalyst solution containing 5500 ppm of molybdenum obtained as described above. The epoxidation reaction is effected at 132° and about 600 psia over a period of approximately 80 minutes, which is sufficient to obtain a tertiary butyl hydroperoxide conversion of 98%, based on the tertiary butyl hydroperoxide charged. The yield of desired propylene oxide product (moles of propylene oxide produced per 100 moles of tertiary butyl hydroperoxide reacted) is 92%.

EXAMPLE VI

A catalyst solution is prepared by blending 2.0 parts of thermally precipitated molybdenum solid as obtained in Example I, above, 36 parts of a solution comprised of about 40% by weight tertiary butyl hydroperoxide in tertiary butyl alcohol, 6.7 parts of propylene glycol, 106 parts of tertiary butyl alcohol and 1.6 parts of oxalic acid dihydrate, and heating the blended mixture at reflux for a period of 2 hours. Thereafter the resultant reaction mixture is filtered to remove any remaining undissolved solids which may be present.

An epoxidation reaction as described in Example V is carried out, employing the above catalyst containing 5500 ppm of molybdenum. The yield of desired propylene oxide is 93%.

Example VI demonstrates the obtainment of improved yields of desired propylene oxide product by use of catalyst compositions of the invention derived from oxalic acid, as compared with typical catalyst compositions disclosed in the prior art devoid of oxalic acid.

EXAMPLE VII

A stainless steel autoclave equipped with a stirrer is charged with 60 parts of propylene, 87.7 parts of a solution comprised of about 40% by weight tertiary butyl hydroperoxide in tertiary butyl alcohol and 2.3 parts of a catalyst solution obtained in Example I above, and containing 11,000 ppm of molybdenum. The epoxidation reaction is effected at 121° and 500 psia over a period of time sufficient to obtain a tertiary butyl hydroperoxide conversion of 98%, based on the tertiary butyl hydroperoxide charged. The yield of desired propylene oxide product is 96%.

An epoxidation reaction as described in this Example VII, above, is carried out, except that the catalyst employed in the epoxidation reaction consists of a catalyst solution containing 5500 ppm of molybdenum, obtained as described above in Example V. The yield of desired propylene oxide product is 95%.

Example VII demonstrates the obtainment of improved yields of desired propylene oxide product by use of catalyst compositions of the invention derived from oxalic acid, as compared with typical catalyst compositions described in the prior art devoid of oxalic acid.

EXAMPLE VIII

An epoxidation catalyst solution is prepared by blending, at room temperature, 50 parts of the catalyst described in Example I, above, and 29 parts of a liquid evaporation residue containing 1.9 weight percent molybdenum obtained by the wiped film evaporation, effected at 400° F. and 1 atmosphere pressure, of a heavy liquid fraction derived from the epoxidation of propylene with tertiary butyl hydroperoxide until 67% of the charge is removed overhead, as described in Example IV of U.S. Pat. No. 3,819,663.

An epoxidation reaction as described in Example VII, above, is carried out while employing the catalyst in concentration of 170 ppm molybdenum. A yield of desired propylene oxide product of 95% is obtained based on the tertiary butyl hydroperoxide charged.

I claim:

1. The process of regenerating a soluble molybdenum composition to obtain a stable catalyst solution capable of being employed as a catalyst in the process for the epoxidation of an olefin with an organic hydroperoxide which comprises thermally precipitating and separating a molybdenum-containing solid containing up to about 50 percent by weight, of molybdenum from a spent catalyst stream obtained from a molybdenum-catalyzed olefin epoxidation reaction, solubilizing said precipitated solid to form a soluble molybdenum composition by contacting at a temperature in the range of from about 20° C. to 130° C. with an admixture comprising a peroxy compound, present in a weight ratio to thermally precipitated solid of 1:2 to 1:20, a mono-hydroxy alcohol present in an amount of at least about 25 parts per part of molybdenum to be solubilized and an organic dicarboxylic acid containing of from 2 to 18 carbon atoms present in an amount of at least about 0.2 parts by weight, per part of molybdenum contained in the solid to be solubilized, and removing any undesired solid material remaining with the said solubilized molybdenum composition.

2. The process of claim 1 wherein said peroxy compound is a member selected from the group consisting of an organic hydroperoxide, an organic peracid and hydrogen peroxide.

3. The process of claim 2 wherein said peroxy compound is an organic hydroperoxide.

4. The process of claim 3 wherein the reaction is additionally carried out in the presence of a polyhydroxy alcohol present in an amount not greater than about 25% by weight, of the monohydroxy alcohol.

5. The process of claim 1 wherein removal of any remaining solid materials is effected by filtration.

6. The process of claim 4 wherein said monohydroxy alcohol is tertiary butyl alcohol.

7. The process of claim 4 wherein said organic dicarboxylic acid is an aliphatic acid containing of from about 2 to 8 carbon atoms.

8. The process of claim 3 wherein said organic dicarboxylic acid is oxalic acid.

9. The process of claim 4 wherein said organic dicarboxylic acid is oxalic acid.

10. The process of claim 9 wherein the proportion by weight of oxalic acid to molybdenum to be solubilized contained in the precipitated solid ranges from between about 0.2:1 to 4:1.

11. The process of claim 10 wherein the monohydroxy alcohol is tertiary butyl alcohol and the polyhydroxy alcohol is propylene glycol.

12. The process of claim 11 wherein said reaction is effected at a temperature in the range of from about 50° C. to 100° C.

13. The process of claim 10 wherein said thermally precipitated molybdenum-containing solid is obtained by admixing said spent catalyst stream with water, in an amount between about 0.5 and 10 percent, based on the weight of the spent catalyst stream, to form an admixture of the spent catalyst stream and water, and heating said admixture to a temperature in the range of about 150° C. to about 250° C. under pressure sufficient to maintain said admixture in the liquid phase and for a time sufficient to precipitate at least a portion of the molybdenum contained in said admixture as a thermally precipitated solid.

14. The process of claim 10 wherein said thermally precipitated molybdenum-containing solid is obtained by heating said spent catalyst solution with from about 5 to about 50 percent by weight of tertiary butyl alcohol to a temperature of between about 100° C. to 300° C. in a closed vessel or under reflux.

* * * * *